United States Patent [19]

Bach

[11] Patent Number: 4,853,547

[45] Date of Patent: Aug. 1, 1989

[54] SYSTEM FOR RADIATION DETECTION USING A GRADED INDEX OPTIC ELEMENT

[75] Inventor: David Bach, Westborough, Mass.

[73] Assignee: Amoco Corporation, Chicago, Ill.

[21] Appl. No.: 85,711

[22] Filed: Aug. 17, 1987

[51] Int. Cl.[4] .......................... G01J 1/58; G01N 21/69
[52] U.S. Cl. ................................ 250/458.1; 250/461.1
[58] Field of Search ............ 250/458.1, 461.1, 231 R, 250/231 P; 350/96.18, 96.25

[56] References Cited

U.S. PATENT DOCUMENTS

| | | | |
|---|---|---|---|
| 4,223,226 | 9/1984 | Quick et al. | 250/458.1 |
| 4,493,212 | 1/1985 | Nelson | 250/231 P |
| 4,498,730 | 2/1985 | Tanaka et al. | 350/96.16 |
| 4,501,970 | 2/1985 | Nelson | 250/461.1 |
| 4,626,693 | 12/1986 | Hirschfeld | 250/458.1 |
| 4,630,923 | 12/1986 | Tans et al. | 356/301 |

FOREIGN PATENT DOCUMENTS 1409196 10/1975 United Kingdom .

OTHER PUBLICATIONS

IBM Technical Disclosure Bulletin, vol. 26, No. 9, pp. 4706–4707, Feb. 1984.
"Graded Index Rod Lenses", Sono, Yamasaki and Kishimoto, NSG America, Inc., Reprint from Laser Focus Mag., Feb. 1981, pp. 70–74.
Selfloc Microlens (SML) NSG American, Inc., Advertising Brochure, Copyright 1984.

Primary Examiner—Janice A. Howell
Assistant Examiner—Tuan Nguyen
Attorney, Agent, or Firm—Bruce A. Walker; William H. Magidson; Ralph C. Medhurst

[57] ABSTRACT

An apparatus and method for delivering excitation radiation to a sample and collecting radiation emanating from the sample. The sample is placed in a deep well which consists of a wall and a bottom end closed by a membrane to form a sample recepticle. A GRIN lens is provided that has a first surface and a second surface, the second surface being inserted into the deep well. A point source of light on the first surface of the GRIN lens is conditioned by the lens and, subsequently, emanates from the second surface of the lens towards the membrane. Reflected, luminescent of fluorescent radiation from the sample is incident on the second surface of the lens, passes through the lens to emanate from the first surface toward collection means, a detector and any desired processing.

22 Claims, 2 Drawing Sheets

SYSTEM FOR RADIATION DETECTION USING A GRADED INDEX OPTIC ELEMENT

BACKGROUND OF THE INVENTION

The present invention relates to an apparatus and a method for delivering radiation to a sample and collecting radiation emanating from the sample and, in particular, where the sample is disposed in a deep well.

A deep well includes a cylindrical receptacle that is open at one end and closed at the opposite end with a membrane. Such a receptacle, or deep well, is useful where a volume of sample and reagent are to be mixed, and the resulting reaction products examined. An examination of the reaction products may be made in the wet state—before drawing the reagent/sample mixture through the membrane, or in the dry-state—after drawing the reagent/sample mixture through the membrane. If the latter, or dry-state, is chosen the membrane serves to filter out the reaction products, leaving them deposited on the surface of the membrane so as to be observed.

One type of examination that can be made of such a sample is an optical one. Optical examination takes advantage of the characteristic of certain analytical samples that, when illuminated by radiation of selected wavelengths, the sample will reflect the radiation or fluoresce in a manner indicative of its composition and/or concentration. This reflected or fluorescent radiation, sometimes referred to as the signal, can be collected and analyzed to provide information about the sample. In the absence of illumination, chemiluminescence radiation can also be collected and analyzed.

Typically, such an optical examination of a sample may be accomplished by a device such as the Dual-Wavelength Thin-Layer Chromato Scanner, Model CS-930 manufactured by the Shimadzu Corporation of Japan. Such devices include a radiation source, which is wavelength selectable, that is formed into an illumination beam and directed towards a sample. A portion of this illumination beam is re-directed to a monitoring photomultiplier to generate a reference signal while the remainder is directed to the sample. Part of the illumination radiation incident on the sample is reflected thereby to a reflection photomultiplier and a second part is transmitted through the sample to a transmission photomultiplier. The signals generated by the photomultipliers can then be analyzed to ascertain the presence and concentration of the chemical constituents of the sample.

Such analytical instruments of the prior art require expensive detectors due to the low collection efficiency of the illumination and detection system. This is due to the spatial relationships of the optical components. These component to air interfaces generate losses of radiation intensity which translate directly to losses of radiation delivered to a sample and signal returned therefrom. This problem is especially acute where samples are disposed in a deep well. Conventional analytical instruments cannot deliver excitation radiation to a point in, or in close proximity to, the sample since the optical components cannot fit within the deep well. Deep wells typically have a depth to diameter ratio greater than 3:1. Similarly, collection of radiation emanating from a sample must be done by such conventional instruments remotely, outside of the deep well.

Providing a bifurcated fiber optic bundle in the deep well to deliver radiation along one or more fibers and return radiation along the remainder of the fibers does not overcome the foregoing disadvantages.

In such a bifurcated bundle, a portion of the return signal is necessarily lost due to focusing inefficiencies and the fact that a portion of the bundle must be dedicated to delivering the illumination radiation, which is not useful for returning the signal. However, for that portion dedicated to returning radiation to a sensing apparatus, the fiber packing density is limited and a portion of the returning radiation will be incident on areas of the fiber optic bundle between individual fibers and, hence, lost.

A further disadvantage of such bifurcated bundles is their tendency to degrade if the epoxy holding the bundle together is subject to chemical attack by the sample or the reagent. In such a case, the bifurcated bundles cannot be cleaned, nor are they sufficiently inexpensive as to be disposable.

SUMMARY OF THE INVENTION

The present invention overcomes the problems and disadvantages of the prior art by providing a method and apparatus which permit the delivery of radiation to a sample in a wet or dry environment in a deep well. Further, radiation emanating from the sample can be collected within the same deep well. Excitation energy can be efficiently delivered to the sample and an efficient collection of energy emanating from the sample can be accomplished. In addition, that portion of the optical system in close proximity to the sample can be easily cleaned or is inexpensive so as to make it disposable and is not subject to degradation as in the case of fiber optic bundles.

Additional objects and advantages of the invention will be set forth in part in the description which follows, and in part will be obvious from the desription, or may be learned by practice of the invention. The objects and advantages of the invention may be realized and attained by means of the instrumentalities and combinations particularly pointed out in the appended claims.

To achieve the objects and in accordance with the purpose of the invention as embodied and broadly described herein, the apparatus for delivering excitation radiation to a sample and collecting radiation emanating from the sample, the sample being disposed in a deep well having an open top end and a wall defining a sample receptacle that is closed at the bottom end thereof by a membrane, comprises: lens means having a first surface and a second surface, the lens means being dimensioned for inserting the second surface into the deep well, the lens means being operative to condition radiation from a point source incident on the first surface to a beam of radiation emanating from the second surface, and operative simultaneously to direct radiation incident on the second surface to the first surface; and collection means disposed substantially adjacent to the first surface for receiving radiation entering the lens means through the second surface and exiting from the lens means through the first surface.

Also to achieve the objects and in accordance with the purpose of the invention as embodied and broadly described herein, the method for delivering excitation radiation to a sample and collecting radiation emanating from the sample, the sample being disposed in a deep well having an open top end and having a wall and a bottom end closed by a membrane to define a sample receptacle, comprises: passing radiation through a lens means having a first surface and an opposing second surface, the lens means being operative to condition radiation from a point source incident on the first surface to a beam of radiation emanating from the second surface, and operative simultaneously to direct radiation incident on the second surface to the first surface; positioning the lens means relative to the deep well such that the second surface is disposed in the sample recepticle opposing the membrane, and collecting the directed radiation exiting the lens means through the first surface.

The accompanying drawings, which are incorporated in and constitute a part of this specification, illustrate one embodiment of the invention, and together with the description serve to explain the principles of the invention.

DESCRIPTION OF THE PREFERRED EMBODIMENT

Reference will now be made in detail to the present preferred embodiments of the invention, examples of which are illustrated in the accompanying drawings.

Figure 1:
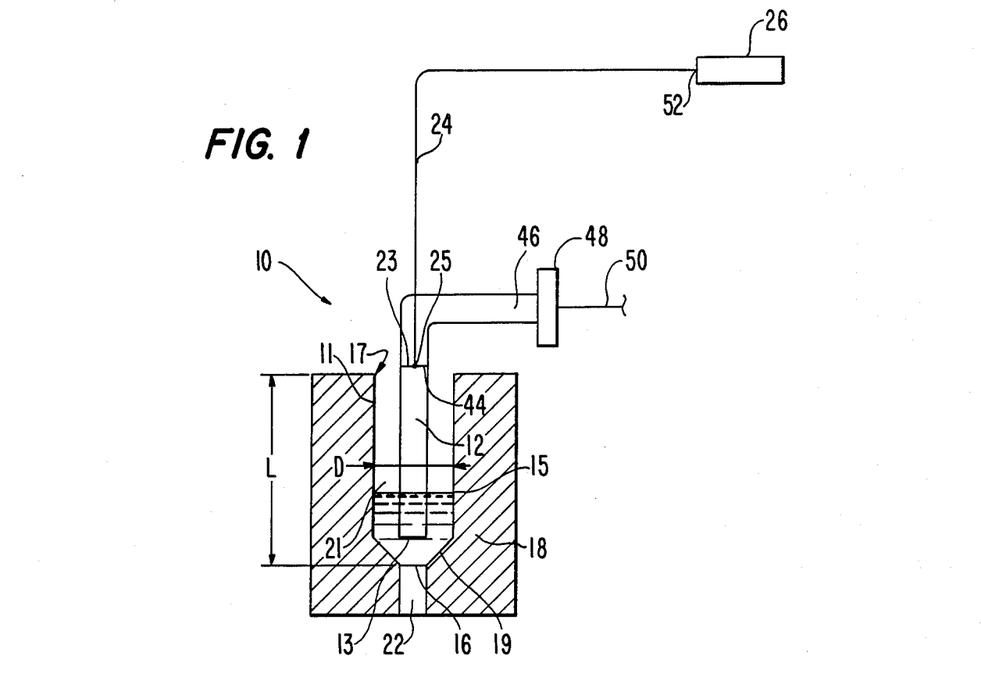
FIG. 1 is a schematic block diagram of the optical components of an analytical instrument constructed in accordance with the present invention.

The preferred embodiment of an apparatus for sampling radiation that is reflected or emitted by a sample disposed in a deep well 18 is shown in FIG. 1 and represented generally by the numeral 10. As used herein, the term "deep well" refers to a receptacle wherein a sample and reagent may be disposed; either one or both of which are in a liquid state. The deep well 18, typically, has a generally cylindrical wall 11 and a bottom end closed by a membrane 16 that defines a sample receptacle 21 within which a sample and/or a reagent may be disposed up to a desired level 15. As shown in FIG. 1 the cylindrical wall 11 may include a tapered portion 19 at the bottom thereof. Such a tapered portion 19 allows the volume of the sample receptacle 21 to be maximized while minimizing the area of a membrane 16. The cylindrical wall 11 extends from a top lip 17 to membrane 16. The membrane 16 is semi-permeable such that the sample/reagent disposed in the sample receptacle 21 may be drawn down through the membrane 16 upon the application of a suction in a passage 22. It can be understood by those skilled in the art that for some analyses it may be desired to analyze the sample/reagent in its wet state. Accordingly, a suitable membrane 16 can be chosen or suction can be withheld from the passage 22 such that the fluid level 15 is maintained.

The embodiments of the invention are described hereinbelow as providing an apparatus to direct radiation to and collect radiation from the surface of membrane 16. It should be understood, however, that the radiation may be reflected by or cause fluorescence or luminescence of a sample or reagent either above the surface or on the surface of the membrane 16.

The apparatus shown in FIG. 1 also includes a point source of radiation 25. As embodied herein the point source of radiation 25 is one end of an optical fiber 24 which is connected at its other end to a radiation source 26. The radiation source 26 is preferably a microlaser and can generate radiation at any desired wavelength. The radiation source 26 further includes conventional means to provide a reference signal, not shown, that is proportional to the intensity of radiation being generated.

It can be understood by those skilled in the art that luminescence occurs and is detected in the absence of radiation. Consequently, the apparatus shown in FIG. 1 is operable to detect luminescence of a sample when the point source 25 is removed or when the radiation source 26 is not generating radiation.

The apparatus also includes lens means 12 for transforming the point source of radiation 25 to a beam of radiation. Preferably, the point source of radiation 25 is optically coupled to a first surface 23 of the lens means 12 and is disposed substantially on the optical axis of the lens means 12. The beam of radiation then emanates from a second surface 13 of the lens means 12 directed towards membrane 16.

As embodied herein the lens means 12 conditions the radiation emanating from the second surface 13 of the lens means 12. Preferably, the lens means 12 causes the radiation emanating from its second surface 13 to be collimated or slight convergent as it propagates towards the membrane 16. Such a preferable embodiment will minimize the amount of radiation reflected by membrane 16, sample or reagent only to be lost by passing outside the aperture defined by the second surface 13.

As embodied herein the lens means 12 is a graded index type lens often referred to as a GRIN lens. A GRIN lens is a cylindrical rod having an index of refraction which decreases as the square of the radial distance from its optical axis. The focusing capability of graded-index lenses comes from a quadratic variation in refractive index with distance from the axis of the fiber segment. This index gradation causes a radiation ray entering the lens initially to be bent toward the axis, then follow a sinusoidal path. The length of graded-index lenses usually is expressed in terms of "pitch", where one unit of pitch corresponds to the distance along the length of the GRIN lens, a ray travels while going through one sinusoidal period. Since, as is known in the art, index of refraction is a function of wavelength, the operation of GRIN lenses, hence their pitch, varies as a function of wavelength.

A GRIN lens with a pitch of 0.25 acts to collimate a point source of radiation, having a desired wavelength, disposed on its entrance face and substantially on its optic axis. A GRIN lens having a pitch of 0.5 will cause an image at its entrance face, comprised of radiation of a desired wavelength, to be relayed in an inverted position to its exit face. An embodiment of the lens means 12 in accordance with the present invention is preferably a GRIN lens having a pitch of 0.25 to 0.50 for the wavelength of the spot source of radiation 25 generated by the radiation source 26. In this way radiation emanating from the exit face 13 of the lens means 12 would either be collimated or convergent. In a more preferred embodiment the lens means 12 is a GRIN lens with a pitch of 0.25. GRIN lenses as utilized in the present invention are available from NSG America, Incorporated of Clark, N.J. and are sold under the trademark SELFOC.

Radiation directed towards the membrane 16 can be reflected or cause the sample to fluoresce. Chemiluminescence can also be induced. This reflected, fluorescent or luminescent radiation is collected by the second surface 13 of the lens means 12. The lens means 12, in the form of a GRIN lens having a pitch of 0.25, acts to collimate any point sources on its second surface 13 and to focus any reflected collimated radiation incident on its second surface 13 to the location of point source 25. Due to the roughness of the membrane 16 and uneven distribution of sample and reagent in solution or on the surface of the membrane 16, the latter phenomenon is deemed to be quite small. That is, a small proportion of the radiation emanating from the sample, reagent or membrane 16 will be incident on the second surface 13 of the lens means 12 in a collimated form to be refocused by the lens means 12 at the location of point source 25, and thereby lost.

A GRIN lens is wavelength dependent. That is, for radiation of a wavelength other than that from the radiation source 26 the pitch of the lens means 12 will be other than 0.25. Accordingly, for fluorescent or luminescent radiation, incident on the second surface 13, the lens means 12 will perform as a GRIN lens having a pitch other than 0.25. The fluorescent or luminescent radiation, therefore, passes back through the lens means 12 to its first surface 23 in a convergent/divergent or collimated state dependent upon the wavelength of the radiation and pitch of the GRIN lens for that particular wavelength.

The apparatus further includes collection means 46 which are proximate to the first surface 23 of the lens means 12 to collect radiation emanating from the first surface 23. The collection means 46 are preferably optic fiber means disposed in an annular fashion about the point source 25 in a manner described below in reference to FIG. 2. At the other end of the optic fiber means a detector 48 is provided for detecting radiation emanating from the first surface 23 of said lens 12 and passing through the bundle of optical fibers 46. A signal line 50 is provided to pass a signal generated by the detector 48 to processing means, not shown.

Figures 2, 2A:
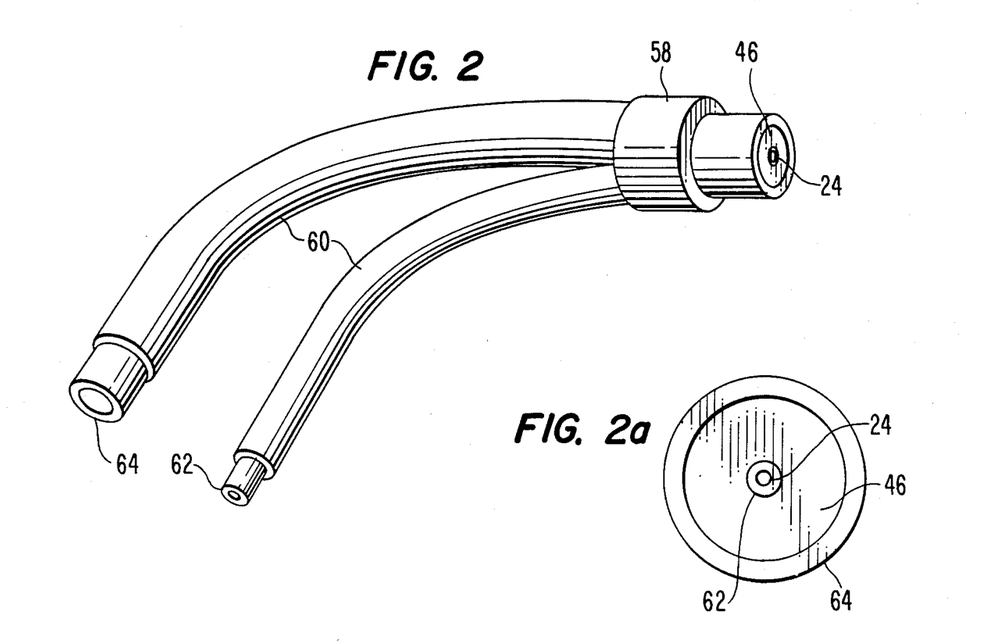
FIG. 2 is a schematic diagram of a bifurcated fiber optic bundle useful in the analytical instruments shown in FIGS. 1, 3 and 4.
FIG. 2A is an end view of the bifurcated optic fiber shown in FIG. 2.

In the preferred embodiment, the point source 25 on the first surface 23 of the lens means 12 and the collection means 46 disposed on the first surface 23 are provided by a bifurcated optic fiber as shown in FIG. 2 and FIG. 2A. The point source 25, not shown in FIG. 2 or FIG. 2A, is provided by a single optic fiber 24, having, for example, a 50 $\mu$diameter, which is surrounded by a cladding layer 62, which has, for example, a 125 $\mu$thickness. The cladding layer 62 is a thin layer of a material having an index of refraction less than that of the core fiber 24. The cladding layer 62 of the single optic fiber 24 is surrounded in an annular fashion by the collection means 46 in the form of optic fiber means. In one embodiment the collection means 46 is a bundle of a plurality of optic fibers. In another embodiment, the collection means is a radiation transmissive liquid contained at one end by the lens means 12 and the other end by the detector 48 comprising what is commonly referred to as a liquid fiber system. The collection means 46 is, preferably, surrounded by a conventional supporting layer 64, typically stainless steel. The supporting layer 64 is usually associated with a jacket 60, typically PVC. A sleeve 58 is provided to maintain support to both the legs of the bifurcated bundle associated with the single fiber 24 and the collection means 46.

Figure 3:
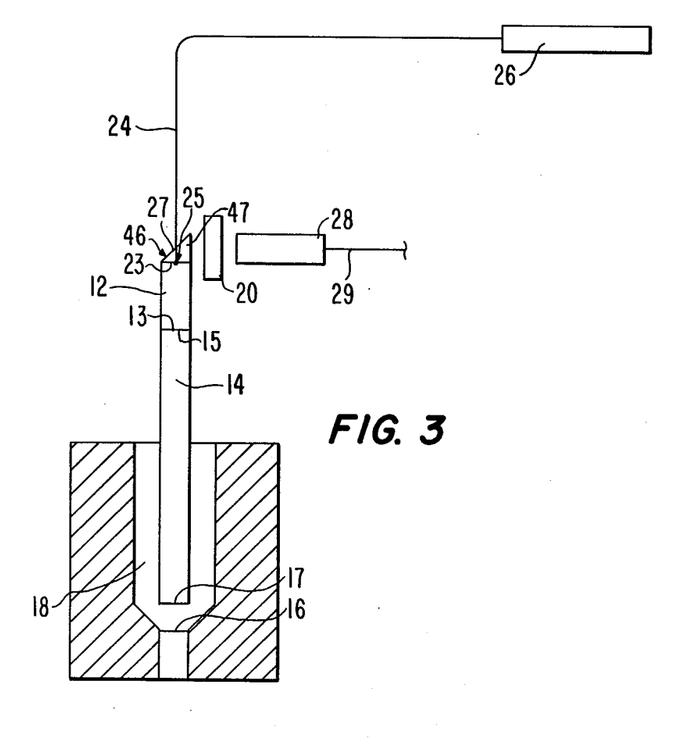
FIG. 3 is a schematic block diagram of the optical components in an analytical instrument constructed in accordance with the present invention.

Another embodiment of the optical components of an analytical detection system in accordance with the present invention is shown in FIG. 3.

As in the embodiment of the invention shown in FIG. 1, the embodiment shown in FIG. 3 includes a point source of radiation 25 and lens means 12. The point source of radiation includes one end of an optic fiber 24 that is optically coupled at the other end to a source 26 of radiation. The point source of radiation 25 is preferably substantially on the optical axis of the lens means 12 and optically coupled to the first surface 23 of the lens means. The lens means 12 itself is preferably a GRIN lens having a pitch of 0.25. In this way the point source of radiation 25 on a first surface 23 of the lens means 12 is substantially collimated when it emanates from the second surface 13 of the lens means 12.

In acordance with the invention, optical relay means 14 are optically coupled to the second surface 13 of the lens means 12. The optical relay means 14 collects substantially all of the radiation emanating from the second surface 13 of the lens means 12. An image, not shown, at a first surface of the optical relay means 14 is transferred to a second surface 17 of the optical relay means 14.

Radiation eminates from the second surface 17 of the optical relay means 14 and is directed towards a membrane 16 disposed in a deep well 18.

The optical relay means 14 is preferably a GRIN lens having a pitch of 0.5 for a desired wavelength. Such an embodiment of the optical relay means 14 transfers and inverts an image at the first surface 15 of the optical relay means 14 to the second surface 17 of the optical relay means 14. Thus, the reach into deep well 18 can be extended beyond that possible with a lens means 12 alone. In this way, an optical system in accordance with the present invention can be used in deep wells having extraordinary depth or where it is desired to place the focused source of radiation closer to the membrane 16. Radiation emanating from the second surface of the optical relay means 14 is directed towards a membrane 16 disposed in a deep well 18 whereupon the radiation is reflected or causes the sample to fluoresce.

Chemiluminescence may also be induced in the sample. This reflected radiation, chemiluminescence or fluoresence is collected by the second surface 17 of the optical relay means 14 whereupon this radiation is transferred from the second surface 17 to the first surface 15 of the optical relay means 14.

For the reasons given hereinabove in reference to the lens means 12 of FIG. 1, the optical relay means 14 will have a pitch other than 0.5 for luminescent or fluorescent radiation which have wavelengths other than that for the radiation from the radiation source 26. Accordingly, reflected, luminescent or fluorescent radiation, incident on the second surface 17 of the optical relay means 14, may be collimated, converged or diverged by the optical relay means 14 depending upon its wavelength, the pitch of the optical relay means 14 for that wavelength and the condition in which the radiation entered the optical relay means 14 at the second surface 17.

It should be understood that the embodiment of the invention shown in FIG. 1, and described in reference thereto, may also include optical relay means 14 as shown in FIG. 3, and described in reference thereto. In such an embodiment of the invention the first face 15 of the optical relay means 14 is optically coupled to the second face 13 of the lens means 12 and the second face 17 of the optical relay means 14 is disposed in the sample receptacle 21.

Returning to FIG. 3, the radiation then emanating from the first surface 15 of the optical relay means 14 is incident on the second surface 13 of the lens means 12. The lens means 12, in the form of a GRIN lens having a pitch of 0.25, conditions radiation passing through it in the same manner described hereinabove in reference to FIG. 1 for the reflected, luminescent and fluorescent radiation passing through it.

FIG. 3 also shows another embodiment of the collection means 46 proximate to the first surface 23 of the lens means 12 to collect radiation emanating from the first surface 23 of the lens means 12. In this embodiment the collection means 46 preferably includes a right angle prism 47 which has one face optically coupled to the first surface 23 of the lens means 12. The hypotenuse face 27 of the right angle prism is disposed substantially in the path of radiation emanating from the first surface 23 and is made totally reflecting such that radiation emanating from the first surface 23 is reflected at a 90° angle from the optic axis of the lens means 12. The radiation thereupon passes through a conventional filter 20 and falls incident on a conventional detector 28. A signal line 29 is provided to pass a signal generated by the detector 28 to conventional processing means, not shown.

In this embodiment the single fiber optic 24 passes through the right angle prism 47 so that the point source of radiation 25 may be optically coupled to the first surface 23 of the lens means as described above.

The filter 20 is selected to pass only that radiation which it is desired to detect. For example, if it is desired to measure the reflectivity of the sample then the filter 20 would be selected to pass only radiation of a wavelength generated by the radiation source 26. If it were desired to sample a specific luminescence or fluorescence radiation wavelength, then an appropriate filter 20 would be selected to pass only that wavelength.

It should also be understood that the embodiment of the collection means 46 shown in FIGS. 1 and 2, and described in reference thereto, can be used in the embodiment of the invention shown in FIG. 3.

It should further be understood that, for the reasons given in reference to FIG. 1, the apparatus shown in FIG. 3 is useful in measuring luminescence of a sample disposed on the membrane 16. During the measurement of such luminescence the point source of radiation 25 may be rendered inoperable by turning off the source of radiation 26 or the point source of radiation 25 may be removed.

Figure 4:
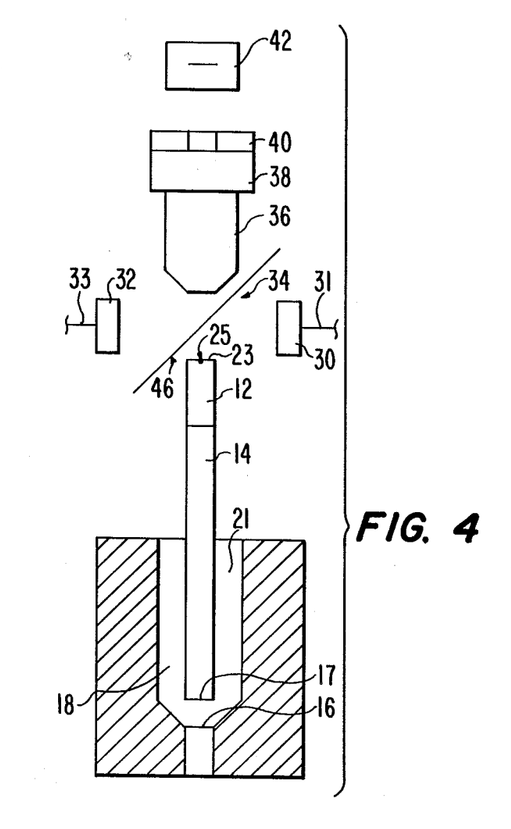
FIG. 4 is a schematic block diagram of the optical components in an analytical instrument constructed in accordance with the present invention.

In accordance with the invention, the point source can also be produced by the apparatus shown in FIG. 4. A source 42, such as a conventional tungsten lamp, produces radiation. The radiation then passes through a conventional aperture 40, a conventional filter 38 to select the wavelength to illuminate the sample, and a conventional microscope objective 36. The microscope objective 36 focuses radiation from the source 42, through a dichroic filter 34, to a point on first surface 23 of the lens means 12. The point 25, so focused on the first surface 23, is located substantially on the optical axis of the lens means 12. The dichroic filter 34 is provided to direct a portion of the beam emanating from the microscope objective 36 onto a reference beam detector 32. In this way, the presence and intensity of the beam from the tungsten source 42 can be sampled.

As discussed hereinabove in reference to the embodiment of the invention illustrated in FIG. 3, the embodiment shown in FIG. 4 provides a lens means 12 to condition the point source 25 to a beam of collimated or converging radiation as it enters the optical relay means 14. The optical relay means 14 is disposed in deep well 18 such that its second face 17 is in the sample chamber 21. The optical relay means 14 relays the image, emanating from the lens means 12, to its second face 17 whereupon the radiation emanates from the second face 17, directed towards the membrane 16. Thus, radiation from the source 42, incident on the first face 23 of the lens means 12, is focussed or collimated by the lens means 12, transferred by optical relay means 14 to its second face 17, and directed towards the membrane 16. Thereupon, radiation reflected by the sample or fluorescence or luminesence from the sample is collected by the optical relay means 14 and transferred to the lens means 12. This reflected, luminescence or fluorescence radiation is then collimated by the lens means 12 and emanates from the first surface 23 of the lens means 12.

In this embodiment of the invention the collection means 46 includes the underside of the dichroic filter 34 which acts to reflect radiation emanating from the first surface 23 towards a detector 30. The detector 30, therefore, detects reflected, luminesence or flluorescence radiation emanating from the sample, reagent or membrane 16. The intensity of the radiation measured by detector 30 can then be compared with the intensity of radiation from reference beam detector 32 so as to provide information concerning the constituent elements in the sample and their relative concentrations. Such a comparison is done in conventional processing means, not shown, which is in communication with the conventional detectors 30 and 32 through communication lines 31 and 33, respectively.

The dichroic mirror 34 may optionally be replaced by a substrate having a first surface and a second surface, both of which are made fully reflecting, and having an aperture therethrough to pass the illumination radiation emanating from the microscope objective 36. Such an aperture is sufficiently small to pass most of the radiation from the microscope objective while allowing a small portion to fall incident on the first reflecting surface of the substrate so as to be reflected to the reference beam detector 32. A beam of radiation emanating from the first face 23 of the lens means 12 is reflected by the second reflecting surface of the substrate to the detector 30.

For the reasons given hereinabove in relation to FIGS. 1 and 3, the point source of light 25 is not necessary during the measurement of luminescence of a sample disposed on the membrane. Consequently, at such times the source 42 may be removed or otherwise disabled so that a spot source of light 25 is not formed on the first surface 23 of the lens means.

It will be apparent to those skilled in the art that various modifications and variations can be made in the apparatus of the present invention and in the point source, the lens means, the optical relay means, the collection means and the interaction between them. For example, the lens means 12 and optical relay means 14 have been described as being GRIN lenses preferably having of a pitch of 0.25 and 0.50, respectively. Other pitches may be chosen if it is desired to provide other than collimated radiation to the sample 16. In addition, the second surface of the lens 13 shown in FIG. 1 may be configured with a concave or convex shape to maximize its collection efficiency. Additionally, such a configuration may be applied to the second surface 17 of the optical relay means 14 in the embodiments of the invention shown in FIGS. 3 and 4. Further, the lens 12 and optical relay means 14, shown in FIGS. 3 and 4 and described in reference thereto, may be combined into a single GRIN optic element having the correct pitch length to both condition and transfer radiation in the manner described. Thus, it is intended that the present invention cover the modifications and variations of this invention provided that they come within the scope of the appended claims and their equivalents.

What is claimed is:

1. An apparatus for delivering excitation radiation to a sample and collecting radiation emanating from the sample, the sample being disposed in a deep well having an open top end and having a wall and a bottom end closed by a membrane to define a sample receptacle, comprising:
   lens means having first surface and an opposing second surface, said lens means being dimensioned for inserting the second surface into the deep well, said lens means being a graded index type lens that is capable of converting radiation from a point source incident on the first surface to a beam of radiation emanating from the second surface with a desired focus, and operative simultaneously to direct radiation incident on said second surface to said first surface;
   collection means disposed substantially adjacent to said first surface for receiving radiation entering said lens means through said second surface and exiting from said lens means through said first surface.

2. An apparatus as claimed in claim 1 that further comprises:
   a point source of radiation on said first surface of said lens means.

3. An apparatus as claimed in claim 2 wherein said lens means converts said point source of radiation into a collimated beam of radiation.

4. An apparatus as claimed in claim 2 wherein said lens means converts said point source of radiation into a converging beam of radiation.

5. An apparatus as claimed in claims 3 or 4 wherein said lens means is a cylindrical rod having an index of refraction which decreases as the square of the radial distance from its optical axis.

6. An apparatus for delivering excitation radiation to a sample and collecting radiation emanating from the sample, the sample being disposed in a deep well having an open top end and having a wall defining a sample receptacle that is closed at the bottom end thereof by a membrane, comprising:
   lens means having a first surface and an opposing second surface, said lens means being a graded index type lens that is capable of converting radiation from a point source incident on the first surface to a beam of radiation emanating from the second surface with a desired focus, and operative simultaneously to direct radiation incident on said second surface to said first surface;
   optical relay means having a third surface and a fourth surface, said third surface being optically coupled to said second surface of said lens means, said optical relay means being dimensioned for inserting the fourth surface into the deep well, said optical relay means relaying an inverted real image from said third surface to said fourth surface and operative simultaneously to direct radiation incident on said fourth surface to said third surface; and
   collection means disposed substantially adjacent to said first surface for receiving radiation entering said optical relay means through said fourth surface and exiting from said lens means through said first surface.

7. An apparatus as claimed in claim 6 that further comprises:
   a point source of radiation on said first surface of said lens means.

8. An apparatus as claimed in claims 1 or 6 which further comprises:
   a right-angle prism having one face thereof optically coupled to said first surface of said lens means;
   fiber optic means;
   a radiation source at a first end of said fiber optic means;
   a second end of said fiber optic means being optically coupled to the first face of said lens means to thereby provide said point source of radiation;
   said right-angle prism having a hole therethrough to pass said fiber optic means;
   the hypotenuse face of said right-angle prism being totally reflecting so as to re-direct radiation emanating from said lens means 90° from the optic axis thereof; and
   detection means disposed in fixed space relation from said prism to detect radiation emanating therefrom.

9. An apparatus as claimed in claims 2 or 7 which further comprises:
   a radiation source;
   a microscope objective disposed between said radiation source and said first surface of said lens to form said point source of radiation;
   a dichroic filter disposed at a 45° angle to the optic axis of said lens means;
   a reference beam detector to detect radiation emanating from said microscope objective reflected by said dichroic filter; and
   a reflection detector to detect radiation emanating from said lens means and reflected by said dichroic filter.

10. An apparatus as claimed in claims 2 or 7 further comprising:
    a single optic fiber coupled at one end thereof to said first surface of said lens means to form said point source of radiation;
    a radiation source at the other end of said single optic fiber;
    optic fiber means disposed annularly about said single optic fiber at the first end thereof and as a circle at the second end thereof; and
    a detector disposed adjacent to the second end of the bundle of optic fibers so as to detect radiation emanating therefrom.

11. An apparatus as claimed in claim 8 wherein said optic fiber means is a bundle of optical fibers.

12. An apparatus as claimed in claim 8 wherein said optic fiber means is a liquid fiber.

13. An apparatus as claimed in claim 7 wherein said lens means converts said point source of radiation into a collimated beam of radiation.

14. An apparatus as claimed in claim 7 wherein said lens means converts said point source of radiation into a diverging beam of radiation.

15. A method for delivering excitation radiation to a sample and collecting radiation emanating from the sample, the sample being disposed in a deep well having an open top end and having a wall and a bottom end closed by a membrane to define a sample receptacle, comprising:

passing radiation through a lens means having a first surface and an opposing second surface, said lens means being a graded index type lens that is capable of converting radiation from a point source incident on said first surface to a beam of radiation emanating from the second surface with a desired focus, and operative simultaneously to direct radiation incident on said second surface to said first surface;

positioning said lens means relative to the deep well such that said second surface is disposed in the sample receptacle opposing the membrane: and collecting the directed radiation exiting the lens means through the first surface.

16. A method as claimed in claim 15 that further comprises:

positioning a point source on said first surface for providing illuminating radiation to the sample in the deep well.

17. A method as claimed in claim 16 wherein the step of passing radiation through a lens means includes utilizing a lens means for converting radiation from a point source to a collimated beam of radiation.

18. A method as claimed in claim 16 wherein the step of passing radiation through a lens means includes utilizing a lens means for conditioning radiation from a point source to a converging beam of radiation.

19. A method for delivering excitation radiation to a sample and collecting radiation emanating from the sample, the sample being disposed in a deep well having an open top end and having a wall defining a sample receptacle that is closed at the bottom end thereof by a membrane, comprising:

passing radiation through a lens means having a first surface and an opposing second surface, said lens means being a graded index type lens that is capable of converting radiation from a point source incident on said first surface to a beam of radiation emanating from the second surface with a desired focus, and operative simultaneously to direct radiation incident on said second surface to said first surface;

passing radiation through an optical relay means, having a third surface and a fourth surface, for relaying an inverted real image from said third surface to said fourth surface and operative simultaneously to direct radiation incident on said fourth surface to said third surface;

optically coupling said second surface of said lens means to said third surface of said optical relay means;

positioning said optical relay means relative to the deep well such that said fourth surface is disposed in the sample receptacle opposing the membrane; and collecting the directed radiation exiting the lens means through the first surface.

20. A method as claimed in claim 19 that further comprises:

positioning a point source on said first surface for providing illuminating radiation to the sample in the deep well.

21. A method as claimed in claim 20 wherein the step of passing radiation through a lens means includes utilizing a lens means for conditioning radiation from a point source to a collimated beam of radiation.

22. A method as claimed in claim 20 wherein the step of passing radiation through a lens means includes utilizing a lens means for conditioning radiation from a point source to a converging beam of radiation.

* * * * *

UNITED STATES PATENT AND TRADEMARK OFFICE
CERTIFICATE OF CORRECTION

PATENT NO.  : 4,853,547
DATED       : August 1, 1989
INVENTOR(S) : David Bach

Page 1 of 3

It is certified that error appears in the above-identified patent and that said Letters Patent is hereby corrected as shown below:

Sheet 1 of 2 of the drawing should be deleted to be replaced with sheet 1 of 2 and sheet 2 of 2 of the drawing as shown on the attached sheets.

Signed and Sealed this

Thirteenth Day of March, 1990

*Attest:*

JEFFREY M. SAMUELS

*Attesting Officer*  *Acting Commissioner of Patents and Trademarks*